United States Patent
Aubart et al.

(10) Patent No.: US 7,456,211 B2
(45) Date of Patent: Nov. 25, 2008

(54) PEPTIDE DEFORMYLASE INHIBITORS

(75) Inventors: Kelly M. Aubart, Collegeville, PA (US);
Jia-Ning Xiang, Palo Alto, CA (US);
Siegfried B. Christensen, IV,
Collegeville, PA (US); Xiangmin Liao,
Collegeville, PA (US); **Maxwell D.
Cummings**, Strafford, PA (US)

(73) Assignee: SmithKline Beecham Corp,
Philadelphia, PA (US)

( * ) Notice: Subject to any disclaimer, the term of this patent is extended or adjusted under 35 U.S.C. 154(b) by 0 days.

(21) Appl. No.: 11/683,089

(22) Filed: Mar. 7, 2007

(65) Prior Publication Data

US 2007/0155792 A1    Jul. 5, 2007

Related U.S. Application Data

(63) Continuation of application No. 11/178,823, filed on Oct. 14, 2005, now abandoned, which is a continuation of application No. 10/469,434, filed as application No. PCT/US02/06258 on Mar. 1, 2002, now abandoned.

(60) Provisional application No. 60/272,446, filed on Mar. 1, 2001.

(51) Int. Cl.
*A61K 31/4015* (2006.01)
*C07D 207/10* (2006.01)

(52) U.S. Cl. ..................... 514/424; 548/541

(58) Field of Classification Search ............... 514/424;
548/400, 530, 541
See application file for complete search history.

(56) References Cited

U.S. PATENT DOCUMENTS 6,495,548 B1 * 12/2002 Duan ...................... 514/231.5

OTHER PUBLICATIONS

*American Family Physician*, 62(3) (Aug. 1, 2000).

* cited by examiner

*Primary Examiner*—Kamal Saeed
*Assistant Examiner*—Janet L Coppins
(74) *Attorney, Agent, or Firm*—Laura K. Madden; Loretta Sauermelch; Mary McCarthy (57) ABSTRACT

The present invention involves novel anti-bacterial compounds represented by Formula (I), pharmaceutical compositions thereof, their use as PDF inhibitors, and their use in the treatment of bacterial infections.

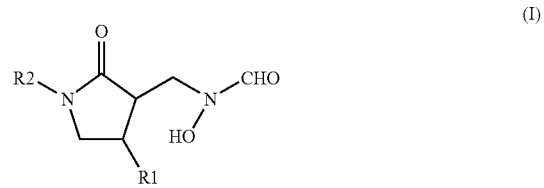

13 Claims, 1 Drawing Sheet

FIGURE 1

PEPTIDE DEFORMYLASE INHIBITORS

This application is a continuation of application Ser. No. 11/178,823, filed Oct. 14, 2005, now abandoned which is a continuation of application Ser. No. 10/469,434, filed Aug. 28, 2003, now abandoned which is a 371 of International Application No. PCT/US02/06258, filed Mar. 1, 2002, which claims benefit of U.S. Provisional Application No. 60/272,446, filed Mar. 1, 2001.

FIELD OF THE INVENTION

The present invention relates to the use of novel anti-bacterial compounds, and pharmaceutical compositions containing these compounds as peptide deformylase inhibitors.

BACKGROUND OF THE INVENTION

Figure 1:
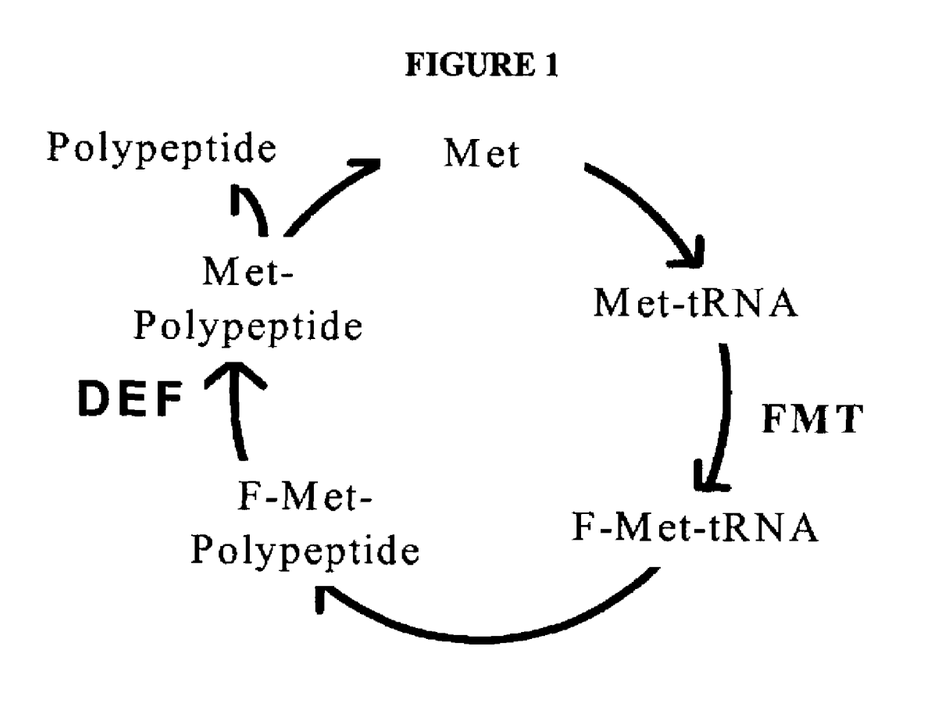
FIG. 1: Provides a graph of the methionine cycle.

Bacterial initiator methionyl tRNA (Met-tRNA) is modified by methionyl tRNA formyltransferase (FMT) to produce formyl-methionyl tRNA (F-Met-tRNA). The formyl methionine (f-met) is then incorporated at the N-termini of newly synthesized polypeptides (F-Met-Polypeptide). Polypeptide deformylase (PDF or Def) then deformylates primary translation products to produce N-methionyl polypeptides (Met-Polypepide). Most intracellular proteins are further processed by methionine amino peptidase (MAP) to yield the mature peptide (or polypeptide) and free methionine (Met), which is recycled. PDF and MAP are both essential for bacterial growth, and PDF is required for MAP activity. This series of reactions is referred to as the methionine cycle (FIG. 1).

To date, polypeptide deformylase homologous genes have been found in bacteria, in chloroplast-containing plants, in mice and in humans. The plant proteins are nuclear encoded but appear to carry a chloroplast localisation signal. This is consistent with the observation that chloroplast RNA and protein synthesis processes are highly similar to those of eubacteria. While there is limited information on protein expression of mammalian PDF gene homologs (Bayer Aktiengesellschaft, Pat. WO2001/42431), no functional role for such proteins has been demonstrated to date (Meinnel, T., Parasitology Today 16(4), 165-168, 2000).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al, 1997, Journal of Molecular Biology, 267, 749-761).

PDF is recognized to be an attractive anti-bacterial target, as this enzyme has been demonstrated to be essential for bacterial growth in vitro (Mazel, D. et al, EMBO J. 13 (4), 914-923, 1994), is not believed to be involved in eukaryotic protein synthesis (Rajagopalan et al, J. Am. Chem. Soc. 119, 12418-12419, 1997), and is universally conserved in prokaryotes (Kozak, M., Microbiol. Rev. 47, 1-45, 1983). Therefore PDF inhibitors can potentially serve as broad spectrum antibacterial agents.

SUMMARY OF THE INVENTION

The present invention involves novel anti-bacterial compounds represented by Formula (I) hereinbelow and their use as PDF inhibitors.

DETAILED DESCRIPTION OF THE INVENTION

The compounds useful in the present methods are selected from Formula (I) hereinbelow:

wherein:
R1 is selected from the group consisting of: $C_{1-6}$alkyl, —$C_{1-2}$alkylAr, and Ar;
R2 is selected ftrom the group consisting of hydrogen, $C_{1-6}$alkyl, —$(CH_2)_mOH$, —$(CH_2)_nAr'$, —$(CH_2)_nHet$, —Ar', —$SO_2R3$, —C(O)R3, —C(O)NHR3, —C(O)OR3, —CH(R4)CONR5R6, and —CH(R4)$CO_2$R7;
R3 is selected from the group consisting of: $C_{1-6}$alkyl, —$C_{1-2}$alkylAr', and Ar';
R4 is hydrogen, or $C_{1-6}$alkyl;
R5 and R6 are independently selected from the group consisting of hydrogen, $C_{1-6}$alkyl, —$C_{1-2}$alkylAr', and Ar'; or R5, R6 together form a five or six membered cycloalkyl ring which is optionally mono-substituted by —$CH_2OR7$;
R7 is selected from the group consisting of hydrogen, and $C_{1-3}$alkyl;
Ar is selected from the group consisting of phenyl, furyl, and thienyl, all of which may be optionally substituted by one or more $Z_1$ groups;
Ar' is selected from the group consisting of: phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl, all of which may be optionally substituted by one or more $Z_2$ groups;
Het is selected from the group consisting of tetrahydrofliranyl and piperidinyl;
$Z_1$ is independently selected from the group consisting of $C_{1-3}$alkyl, —CN, F, Cl, Br, and I;
$Z_2$ is independently selected from the group consisting of $C_{1-6}$alkyl, —OR2, —$(CH_2)_nCO_2R4$, —C(O)NR5R6, —CN, —$(CH_2)_nOH$, —$NO_2$, F, Cl, Br, I, —NR5R6, and —NHC(O)R1;
m is 2 to 5;
and
n is 0 to 5.

As used herein, "alkyl" refers to a hydrocarbon group joined together by single carbon-carbon bonds. The alkyl hydrocarbon group may be linear, branched or cyclic.

Preferred compounds useful in the present invention are selected from the group consisting of:
(3S,4R)-N-[4-Butyl-1-(5-hydroxypentyl)-2-oxopyrrolidin-3-yl-methyl]-N-hydroxyformamide;
(3R,4S)-N-[4-Butyl-1-(5-hydroxypentyl)-2-oxopyrrolidin-3-yl-methyl]-N-hydroxyformamide;
(+/−)-(3RS,4SR)-N-[4-Butyl-2-oxo-1-(t-butylcarboxy)pyrrolidin-3-yl-methyl]-N-hydroxyformamide;

(+/−)-(3RS,4SR)-N-(4-Butyl-2-oxopyrrolidin-3-yl-methyl)-N-hydroxyformamide;

(+/−)-(3RS,4SR)-N-(4-Butyl-2-oxo-1-pentanoylpyrrolidin-3-yl-methyl)-N-hydroxyformamide;

(+/−)-(3RS,4SR)-N-[4-Butyl-2-oxo-1-(2-phenylethanoyl)pyrrolidin-3-yl-methyl]-N-hydroxyformamide;

(+/−)-(3RS,4SR)-N-[4-Butyl-2-oxo-1-(1-phenylmethanoyl)pyrrolidin-3-yl-methyl]-N-hydroxyformamide;

(+/−)-(3RS,4SR)-N-(1-Benzenesulfonyl-4-butyl-2-oxopyrrolidin-3-yl-methyl)-N-hydroxyformamide;

(+/−)-(3RS,4SR)-N-[1-(Butane-1-sulfonyl)-4-butyl-2-oxopyrrolidin-3-yl-methyl]-N-hydroxyformamide;

(+/−)-(3RS,4SR)-N-[4-Butyl-1-(naphthalen-2-ylmethanoyl)-2-oxopyrrolidin-3-yl-methyl]-N-hydroxyformamide;

(+/−)-(3RS,4SR)-N-(1-Benzyl-4-butyl-2-oxopyrrolidin-3-yl-methyl)-N-hydroxyformamide;

(+/−)-(3RS,4SR)-N-{4-Butyl-1-[1-(4-ethoxyphenyl)methanoyl]-2-oxopyrrolidin-3-yl-methyl}-N-hydroxyformamide;

(+/−)-(3RS,4SR)-N-{4-Butyl-1-[1-(3-ethoxyphenyl)methanoyl]-2-oxopyrrolidin-3-yl-methyl}-N- hydroxyformamide;

(+/−)-(3RS,4SR)-N-{4-Butyl-1-[1-(2-ethoxyphenyl)methanoyl]-2-oxopyrrolidin-3-yl-methyl}-N- hydroxyformamide;

(+/−)-(3RS,4SR)-N-(4-Butyl-2-oxo-1-pyridin-3-ylmethylpyrrolidin-3-yl-methyl)-N-hydroxyformamide;

N-((3S,4R)-4-Butyl-1-{(S)-1-[1-((S)-2-methoxymethylpyrrolidin-1-yl)methanoyl]-3-methylbutyl}-2-oxopyrrolidin-3-yl-methyl)-N-hydroxyformamide;

N-((3R,4S)-4-Butyl-1-{(S)-1-[1-((S)-2-methoxymethylpyrrolidin-1-yl)methanoyl]-3-methylbutyl}-2-oxopyrrolidin-3-yl-methyl)-N-hydroxyformamide;

N-((3S,4R)-4-Butyl-1-{(S)-1-[1-(dimethylamino)methanoyl]-3,3-dimethylbutyl}-2-oxopyrrolidin-3-yl-methyl)-N-hydroxyformamide;

(+/−)-(3RS,4SR)-N-[4-Butyl-1-(4-ethoxybenzyl)-2-oxopyrrolidin-3-yl-methyl]-N-hydroxyformamide;

(+/−)-(3RS,4SR)-N-[4-Butyl-1-(4-hydroxybenzyl)-2-oxopyrrolidin-3-yl-methyl]-N-hydroxyformamide;

(+/−)-(3RS,4SR)-N-{4-Butyl-1-[4-(2-morpholin-4-yl-2-oxoethoxy)benzyl]-2-oxopyrrolidin-3-yl-methyl}-N-hydroxyformamide;

(+/−)-(3RS,4SR)-N-{4-Butyl-1-[4-(4-carboxy-1-butoxy)benzyl]-2-oxopyrrolidin-3-yl-methyl}-N-hydroxyformamide;

(+/−)-(3RS,4SR)-N-{4-Butyl-1-[4-(3-hydroxybenzoxy)benzyl]-2-oxopyrrolidin-3-yl-methyl}-N-hydroxyformamide;

(+/−)-(3RS,4SR)-N-{4-Butyl-2-oxo-1-[4-(tetrahydrofuran-2-ylmethoxy)benzyl]-pyrrolidin-3-yl-methyl}-N-hydroxyformamide;

(+/−)-(3RS,4SR)-N-{4-Butyl-1-[4-(furan-2-ylmethoxy)benzyl]-2-oxopyrrolidin-3-yl-methyl}-N-hydroxyformamide;

(+/−)-(3RS,4SR)-N-{4-Butyl-1-[4-(3-hydroxypropoxy)benzyl]-2-oxopyrrolidin-3-yl-methyl}-N-hydroxyformamide;

(+/−)-(3RS,4SR)-N-{4-Butyl-2-oxo-1-[4-(piperidin-3-yl-methoxy)benzyl]pyrrolidin-3-yl-methyl}-N-hydroxyformamide;

(+/−)-(3RS,4SR)-N-{4-Butyl-2-oxo-1-[4-(pyridin-3-yl-methoxy)benzyl]pyrrolidin-3-yl-methyl}-N-hydroxyformamide;

(+/−)-(3RS,4SR)-N-{4-Butyl-1-[4-(5-hydroxypentoxy)benzyl]-2-oxopyrrolidin-3-yl-methyl}-N-hydroxyformamide; and (+/−)-(3RS,4SR)-N-[4-Butyl-1-(2,3-dichlorobenzyl)-2-oxopyrrolidin-3-yl-methyl]-N-hydroxyformamide;

(+/−)-(3RS,4SR)-N-[4-Butyl-1-(3,4-dichlorobenzyl)-2-oxopyrrolidin-3-yl-methyl]-N-hydroxyformamide;

(+/−)-(3RS,4SR)-N-[4-Butyl-2-oxo-1-phenylpyrrolidin-3-y-methyl]-N-hydroxyformamide;

(+/−)-(3RS,4SR)-N-{4-Butyl-1-[2-(2-hydroxyphenyl)-2-oxoethyl]-2-oxopyrrolidin-3-yl-methyl}-N-hydroxyformamide;

(+/−)-(3RS,4SR)-N-[4-Butyl-1-(3,5-dimethylisoxazol-4-yl-methyl)-2-oxopyrrolidin-3-yl-methyl]-N-hydroxyformamide;

(+/−)-(3RS,4SR)-N-[4-Butyl-1-(2-methylthiazol-4-ylmethyl)-2-oxopyrrolidin-3-yl-methyl]-N-hydroxyformamide.

Also included in the present invention are pharmaceutically acceptable salts and complexes, such as the hydrochloride, hydrobromide and trifluoroacetate salts, and the sodium, potassium, and magnesium salts. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

The present invention provides compounds of formula (I):

(I)

that can be prepared by a process consisting of:
treating an aldehyde of Formula (2)

R1CHO (2)

with Ph₃P=CHCO₂Et in a solvent, such as tetrahydrofuran, to give an α,β-unsaturated ester of Formula (3).

(3)

Treatment of a compound of Formula (3) with nitromethane in the presence of Triton B leads to a Michael addition product of Formula (4).

(4)

Reduction of the nitro group in a compound of Formula (4) under hydrogenolysis conditions followed by an intramo- lecular cyclization, at appropriate temperature in an appropriate solvent, such as toluene, affords a lactam of Formula (5).

(5)

A compound of Formula (5) can be converted to a compound of Formula (6) wherein R2 is other than H through an alkylation reaction.

(6)

Treatment of an enolate generated from a lactam of Formula (6) with an appropriate formylating agent, such as isopropyl formate, in an appropriate solvent, such as dry tetrahydrofuran, affords an aldehyde of Formula (7).

(7)

Coupling of an aldehyde of Formula (7) with a suitable reagent, such as benzyloxyamine hydrochloride, in a suitable solvent, such as dry pyridine, affords a compound of Formula (8).

(8)

Reduction of a compound of Formula (8) with a suitable reagent, such as sodium cyanoborohydride, in an appropriate solvent, such as acetic acid, affords a compound of Formula (9).

(9)

Formylation of a compound of Formula (9) with a suitable reagent, such as formyl acetyl anhydride, in a suitable solvent, such as methylene chloride, affords a compound of Formula (10).

(10)

Removal of the protecting group(s) in a compound of Formula (10) affords a compound of Formula (I).

Alternatively, the lactam nitrogen of a compound of Formula (5) can be protected using an appropriate protecting group, such as a Boc group, under standard conditions to give a versatile intermediate of Formula (11).

(11)

Conversion of a lactam of Formula (11) to the α-formyl lactam of Formula (12) can be achieved by treatment of an enolate generated from a lactam of Formula (11) with an appropriate formylating agent such as isopropyl formate, or alternatively, by using Bredereck's reagent followed by acidic hydrolysis.

(12)

Alternatively, a compound of Formula (12) can be derived from the Boc-protected α,β-unsaturated pyrrolidinone (13) through 1,4-addition with an organometallic reagent, such as R1MgX, followed by quenching with an electrophile, such as isopropyl formate or methyl bromoacetate.

(13)

Reductive amination of an aldehyde of Formula (12) with sodium cyanoborohydride and an amine, such as benzyloxyamine, in a suitable solvent provides an amine of Formula (14).

(14)

Treatment of a compound of Formula (14) with formic acid in the presence of acetic anhydride and triethylamine provides a compound of Formula (15).

(15)

Removal of the Boc group compounds of Formula (15) using an appropriate acid, such as trifluoroacetic acid, gives a compound of Formula (16).

(16)

A lactam of Formula (16) is then readily converted to the target compound of Formula (I) by treatment with an alkyl halide, a sulfonyl chloride, an acid chloride or an isocyanate followed by deprotection of the benzyl group under hydrogenolysis conditions.

Alternatively, treating an unsaturated lactone of Formula (17)

(17)

with, e.g., a Grignard reagent R1MgX in the presence of catalytic ammount of a copper salt, such as copper (I) bromide, HMPA and chlorotrimethylsilane at an appropriate temperature, affords a lactone of Formula (18).

(18)

Treatment of a lactone of Formula (18) with an amine of Formula (19)

R2-NH$_2$ (19)

in a suitable solvent, such as toluene in the presence of a Lewis acid, such as AlMe$_3$, followed by an intramolecular cyclization under Mitsunobu conditions, affords a lactam of Formula (6).

Alternatively, the lactone ring in a compound of Formula (18) can be hydrolyzed using appropriate base, such as sodium hydroxide. The resulting carboxylate is then coupled with an amine of Formula (19) followed an intramolecular cyclization to afford a lactam of Formula (6).

Alternatively, a lactone of Formula (18) is treated with a base, such as lithium diisopropylamine, and chloromethyl benzyl ether to give a compound of Formula (20).

(20)

A lactone of Formula (20) is then converted to a lactam of Formula (21) under similar conditions described above for conversion of a compound of Formula (18) to a compound of Formula (6).

(21)

Removal of the benzyl group in a compound of Formula (21) followed by oxidation of the alcohol using an appropriate oxidant, such as Dess-Martin reagent, affords an aldehyde of Formula (7).

An optically active compound of Formula (I) can be prepared by treating a lactone of Formula (18) with a chiral amine, such as (S)-methylphenyl amine, in the presence of a catalyst, such as 2-hydroxypyridine, in a suitable solvent, such as toluene, at reflux to afford a mixture of two diastereomers of Formula (22) and (23), which can be readily separated by silica gel flash column chromatography.

Intramolecular Mitsunobu reaction of a compound of Formula (22) or (23), followed by removal of the N-protecting group with sodium in liquid animonia affords an optically pure lactam of formula (24) or (25), respectively.

Conversion of a chiral lactam of Formula (24) or (25) to the chiral target compound of Formula (I) can then be achieved using reagents and conditions described above for transformation of a compound of Formula (5) to a compound of Formula (I).

Alternatively, treatment of a compound of Formula (22) or (23) with an appropriate acid, e.g., 1 M $H_2SO_4$, in an appropriate solvent, such as dioxane, affords a chiral lactone of Formula (26) or (27), respectively.

Using reagents and conditions described above for transformation of a compound of Formula (18) to a compound of Formula (I), a chiral lactone of Formula (26) or (27) can then be converted to the chiral target compound of Formula (I).

The present compounds are further exemplified by the following Examples which are intended to be illustrative of the present invention and not limiting in any way.

EXAMPLE 1

Preparation of N-[(3S,4R)-4-Butyl-1-(5-hydroxypentyl)-2-oxopyrrolidin-3-yl-methyl]-N-hydroxyformamide 1(a) (R)-3-Hydroxymethylheptanoic acid, (S)-1-phenylethylamide A mixture of (+/−)-4-butyldihydrofuran-2-one (3.9 g, 27.4 mmol), 2-hydroxypyridine (3.1 g, 32.9 mmol) and (S)-1-phenylethylamine (7.8 mL, 60.3 mmol) in dry toluene (50 mL) was heated to reflux overnight. The reaction mixture was cooled to room temperature and diluted with ethyl acetate (100 mL), washed with 1 N HCl (2×50 mL) and brine (50 mL), dried ($Na_2SO_4$), and concentrated. The residue was purified by flash column chromatography (silica gel, 4:1 EtOAc/hexanes) to afford two compounds as white solids. The first eluted fraction was (S)-3-hydroxymethylheptanoic acid, (S)-1-phenylethylamide (2.8 g, 39%) which is used in Example 2. $^1$H NMR (CDCl$_3$) δ 7.33 (m, 5 H), 6.07 (bs, 1 H), 5.11 (q, 1 H), 3.63 (m, 1 H), 3.48 (m, 1 H), 3.29 (bs, 1 H), 2.29 (m, 2 H), 1.95 (m, 1 H), 1.50 (d, 2 H), 1.28 (m, 6 H), 0.88 (t, 3 H). MS(ES) m/e 264 [M+H]$^+$. The second eluted fraction (R)-3-hydroxymethylheptanoic acid, (S)-1-phenylethylamide (2.6 g, 36%). $^1$H NMR (CDCl$_3$) δ 7.29 (m, 5 H), 6.34 (bs, 1 H), 5.09 (q, 1 H), 3.64 (m, 1 H), 3.57 (bs, 1 H), 3,48 (m, 1 H), 2.28 (m, 2 H), 1.93 (m, 1 H), 1.48 (d, 2 H), 1.28 (m, 6 H), 0.88 (t, 3 H). MS(ES) m/e 264 [M+H]$^+$.

1(b) (R)-4-Butyl-1-[(S)-1-phenylethyl]pyrrolidin-2-one

To a solution of di-t-butyl azodicarboxylate (2.1 g, 9.1 mmol) in tetrahydrofuran (25 mL) under argon was added tributylphosphine (2.27 mL, 9.1 mmol). The mixture was stirred for 5 minutes and was added slowly to a solution of (R)-3-hydroxymethylheptanoic acid, (S)-1-phenylethylamide (1.84 g, 7.0 mmol) in dry THF (10 mL) at 0° C. The reaction was warmed up to rt and stirred overnight. Saturated NaHCO$_3$ (100 mL) was added and the resulting mixture was extracted with CH$_2$Cl$_2$ (2×100 mL). The combined organic extracts were dried (Na$_2$SO$_4$), filtered and concentrated. The residue was purified by flash column chromatography (silica gel, 1:4 EtOAc/hexanes) to afford 1.4 g (82%) of (R)-4-butyl-1-[(S)-1-phenylethyl]pyrrolidin-2-one as a colorless oil: $^1$H NMR (CDCl$_3$) δ 7.33 (m, 5 H), 5.48 (q, 1 H), 3.06 (t, 1 H), 2.92 (t, 1 H), 2.53 (q, 1 H), 2.06 (m, 2 H), 1.51 (d, 3 H), 1.20-1.46 (m, 6 H), 0.88 (t, 3 H). MS(ES) m/e 246 [M+H]$^+$.

1(c) (R)-4-Butylpyrrolidin-2-one

To a solution of (R)-4-butyl-1-[(S)-1-phenylethyl]pyrrolidin-2-one (1.4 g, 5.7 mmol) in dry tetrahydrofuran (10 mL) at −78° C. was added condensed liquid ammonia (100 mL). Freshly cut sodium (0.66 g, 28.5 mmol) was added and the resulting mixture was stirred at −78° C. for 2 h. The reaction was quenched with solid ammonium chloride. Ammonia was evaporated by warming up the reaction mixture slowly to room temperature. Water (50 mL) was added and the mixture was extracted with ethyl acetate (3×50 mL). The combined organic extracts were dried (Na$_2$SO$_4$), filtered and concentrated. The residue was purified by flash column chromatography (silica gel, 4:1 EtOAc/acetone) to afford 0.7 g (87%) of (R)-4-butylpyrrolidin-2-one as a colorless oil: [α]$_D$=+0.95° (c=0.60, CH$_2$Cl$_2$) {lit. [α]$_D$=−0.67° (c=0.60, CH$_2$Cl$_2$) for (S)-enantiomer, Meyers, A. I. and Snyder, L. 1993, J. Org. Chem. 58, 36-42}; $^1$H NMR (CDCl$_3$) δ 6.07 (bs, 1 H), 3.48 (t, 1 H), 3.02 (t, 1 H), 2.45 (m, 2 H), 1.99 (m, 1 H), 1.22-1.50 (m, 6 H), 0.90 (t, 3 H). MS(ES) m/e 142 [M+H]$^+$.

1(d) (R)-1-(5-Benzyloxypentyl)-4-butylpyrrolidin-2-one

To a solution of (R)-4-butylpyrrolidin-2-one (0.42 g, 2.9 mmol) in dry dimethylformamide (10 mL) under argon was slowly added sodium hydride (60% in mineral oil, 0.14 g, 3.5 mmol) at 0° C. After stirring at 0° C. for 30 minutes, 5-benzyloxypentyl bromide (0.9 g, 3.5 mmol) was added dropwise. The resulting mixture was stirred at room temperature overnight and then diluted with ethyl acetate (50 mL). The organic solution was washed with water (4×30 mL) and brine (30 mL), dried (Na$_2$SO$_4$) and concentrated. The residue was purified by flash column chromatography (silica gel, 1:1 EtOAc/hexanes) to afford 0.73 g (95%) of (R)-1-(5-benzyloxypentyl)-4-butylpyrrolidin-2-one as a colorless oil: $^1$H NMR (CDCl$_3$) δ 7.33 (m, 5 H), 4.51 (s, 2 H), 3.45 (m, 3 H), 3.27 (t, 2 H), 2.99 (dd, 1 H), 2.52 (dd, 1 H), 2.32 (m, 1 H), 2.06 (m, 1 H), 1.24-1.71 (m, 12 H), 0.93 (t, 3 H). MS(ES) m/e 318 [M+H]$^+$.

1(e)[(3S,4R)-3-(Benzyloxyaminomethyl)-1-(5-benzyloxypentyl)-4-butyl-pyrrolidin-2-one A solution of (R)-1-(5-benzyloxypentyl)-4-butylpyrrolidin-2-one (0.25 g, 0.79 mmol) in dry THF (3 mL) was slowly added to a 2 M solution of lithium diisopropylamide (0.47 mL, 0.94 mmol) in THF (2 mL) at −78° C. under argon. The reaction mixture was stirred at the same temperature for 1 h. Isopropyl fornate (0.047 mL, 0.94 mmol) was then added dropwise. The resulting mixture was stirred for 3 h and then quenched with saturated ammonium chloride (10 mL). The mixture was extracted with ethyl acetate (3×10 mL) and the combined organic extracts were dried (Na$_2$SO$_4$), filtered, and concentrated. The residue was dissolved in dry pyridine (5 mL), and treated with benzyloxyamine hydrochloride (0.13 g, 0.79 mmol) at room temperature for 2 h. After removing the solvent under reduced pressure, the residue was dissolved in acetic acid (5 mL) and treated with NaCNBH$_3$ (0.22 g, 1.03 mmol) at room temperature for 2 h. The mixture was diluted with ethyl acetate (10 mL) and neutralized with 10% aqueous NaOH. The organic phase was separated, washed with brine, dried (Na$_2$SO$_4$), and concentrated. The residue was purified by HPLC to give 0.11 g (31%) of [(3S,4R)-3-benzyloxyaminomethyl)-1-(5-benzyloxypentyl)-4-butyl-pyrrolidin-2-one as a colorless oil: $^1$H NMR (CDCl$_3$) δ 7.32 (m, 10 H), 6.45 (bs, 1 H), 4.72 (s, 2 H), 4.51 (s, 2 H), 3.47 (t, 2 H), 3.39 (t, 1 H), 3.06-3.33 (m, 4 H), 2.93 (t, 1 H), 2.43 (m, 1H), 2.03 (m, 1 H), 1.23-1.73 (m, 12 H), 0.93 (t, 3 H). MS(ES) m/e 453 [M+H]$^+$.

1(f) N-[(3S,4R)-4-Butyl-1-(5-hydroxypentyl)-2-oxopyrrolidin-3-yl-methyl]-N-hydroxyformamide A mixture of formic acid (0.011 mL, 0.29 mmol) and acetic anhydride (0.026 mL, 0.28 mmol) was heated to 50° C. for 1 h. To this mixture at room temperature was added a mixture of [(3S,4R)-3-(benzyloxyaminomethyl)-1-(5-benzyloxypentyl)-4-butyl-pyrrolidin-2-one (65 mg, 0.14 mmol) and triethylamine (0.02 mL, 0.18 mmol) in methylene chloride (3 mL). The resulting mixture was stirred at room temperature for 30 minutes. The reaction was diluted with methylene chloride (5 mL) and quenched with water (5 mL). The organic phase was washed with brine (5 mL), dried (Na$_2$SO$_4$), filtered, and concentrated. The residue was dissolved in methanol (3 mL) and stirred under a hydrogen balloon in the presence of palladium on activated carbon (40 mg) for 4 h. The reaction mixture was filtered, concentrated, and the residue was purified by HPLC to afford 25 mg (58%) of N-[(3S,4R)-4-butyl-1-(5-hydroxypentyl)-2-oxopyrrolidin-3-yl-methyl]-N-hydroxyformamide as a colorless glass: $^1$H NMR (CD$_3$OD) δ 8.33 (s, 0.5 H), 7.98 (s, 0.5 H), 3.80 (m, 1 H), 3.57 (m, 3 H), 3.33 (m, 3 H), 3.07 (t, 1H), 2.55 (m, 1 H), 2.12-2.26 (m, 1H), 1.33-1.71 (m, 12 H), 0.94 (t, 3 H). MS(ES) m/e 301 [M+H]$^+$.

EXAMPLE 2

Preparation of N-[(3R,4S)-4-Butyl-1-(5-hydroxypentyl)-2-oxopyrrolidin-3-yl-methyl]-N-hydroxyformamide Following the procedure of Example 1(a)-1(f), except substituting (R)-1-(5-benzyloxypentyl)-4-butylpyrrolidin-2-one with (S)-1-(5-benzyloxypentyl)-4-butylpyrrolidin-2-one, the title compound was prepared. It has the identical $^1$H NMR and MS as the compound of Example 1(f).

EXAMPLE 3

Preparation of (+/−)-(3RS,4SR)-N-(1-Benzyl-4-butyl-2-oxopyrrolidin-3-yl-methyl)-N-hydroxyformamide 3(a) 4-Butylpyrrolidin-2-one To a solution of 3-nitromethylheptanoic acid ethyl ester (10 g, 49.2 mmol) in methanol (100 mL) under argon was added Raney Ni (5 g). The mixture was stirred under 50 psi of hydrogen for 48 h, flushed with argon, filtered through a Celite pad, and concentrated under vacuum to afford 4-butylpyrrolidin-2-one as a colorless oil (6.3 g, 91%). MS(ES) m/e 142 [M+H]$^+$.

3(b) (+/−)-(3RS,4SR)-N-(1-Benzyl-4-butyl-2-oxopyrrolidin-3-yl-methyl)-N-hydroxyformamide Following the procedure of Example 1(d)-1(f), except substituting compound (R)-4-butylpyrrolidin-2-one with 4-butylpyrrolidin-2-one, and substituting 5-benzyloxypentyl bromide with benzyl bromide, (+/−)-(3RS,4SR)-N-(1-benzyl-4-butyl-2-oxopyrrolidin-3-ylmethyl)-N-hydroxyformamide was prepared as a colorless oil. MS(ES) m/e 305 [M+H]$^+$.

Proceeding in a similar manner, except substituting appropriate intermediates for the benzyl bromide above, the following compounds were synthesized:

(+/−)-(3RS,4SR)-N-(4-Butyl-2-oxo-1-pyridin-3-ylmethylpyrrolidin-3-yl-methyl)-N-hydroxyformamide. MS(ES) m/e 306 [M+H]$^+$.

(+/−)-(3RS,4SR)-N-[4-Butyl-1-(4-ethoxybenzyl)-2-oxopyrrolidin-3-yl-methyl]-N-hydroxyformamide. MS(ES) m/e 349 [M+H]$^+$.

(+/−)-(3RS,4SR)-N-[4-Butyl-1-(2,3-dichlorobenzyl)-2-oxopyrrolidin-3-yl-methyl]-N-hydroxyformamide. MS(ES) m/e 373 [M+H]+.

(+/−)-(3RS,4SR)-N-[4-Butyl-1-(3,4-dichlorobenzyl)-2-oxopyrrolidin-3-yl-methyl]-N-hydroxyformamide. MS(ES) m/e 373 [M+H]+.

(+/−)-(3RS,4SR)-N-[4-Butyl-1-(3,5-dimethylisoxazol-4-yl-methyl)-2-oxopyrrolidin-3-yl-methyl]-N-hydroxyformamide. MS(ES) m/e 324 [M+H]+.

(+/−)-(3RS,4SR)-N-[4-Butyl-1-(2-methylthiazol-4-yl-methyl)-2-oxopyrrolidin-3-yl-methyl]-N-hydroxyformamide. MS(ES) m/e 326 [M+H]+.

EXAMPLE 4

Preparation of (+/−)-(3RS,4SR)-N-[4-Butyl-1-(4-hydroxybenzyl)-2-oxopyrrolidin-3-yl-methyl]-N-hydroxyformamide 4(a) (+/−)-(3RS,4SR)-N-[1-(4-Allyloxybenzyl)-4-butyl-2-oxopyrrolidin-3-yl-methyl]-N-benzyloxyformamide Following the procedure of Example 1(d)-1(f), except substituting compound (R)-4-butylpyrrolidin-2-one with the compound of Example of 3(a), and 5-benzyloxypentyl bromide with 4-allyloxybenzyl bromide, (+/−)-(3RS,4SR)-N-[1-(4-allyloxybenzyl)-4-butyl-2-oxopyrrolidin-3-yl-methyl]-N-benzyloxyformamide was prepared as a colorless oil. MS(ES) m/e 451 [M+H]+.

4(b) (+/−)-(3RS,4SR)-N-Benzyloxy-N-[4-butyl-1-(4-hydroxybenzyl)-2-oxopyrrolidin-3-yl-methyl]formamide To a solution of (+/−)-(3RS,4SR)-N-[1-(4-allyloxybenzyl)-4-butyl-2-oxopyrrolidin-3-yl-methyl]-N-benzyloxyformamide (2.6 g, 5.77 mmol) in dichloromethane (60 mL) under argon was added morpholine (6 mL), water (1.2 mL) and then tetrakis(triphenylphosphine)palladium (0.33 g, 0.28 mmol). The reaction mixture was stirred at rt for 1 h, filtered through a Celite pad and concentrated. The residue was purified by flash column chromatography (silica gel, ethyl acetate/hexanes 4:1) to afford (+/−)-(3RS,4SR)-N-benzyloxy-N-[4-butyl-1-(4-hydroxybenzyl)-2-oxopyrrolidin-3-yl-methyl]formamide as a white solid (2.1 g, 88%). MS(ES) m/e 411 [M+H]+.

4(c) (+/−)-(3RS,4SR)-N-[4-Butyl-1-(4-hydroxybenzyl)-2-oxopyrrolidin-3-yl-methyl]-N-hydroxyformamide (+/−)-(3RS,4SR)-N-Benzyloxy-N-[4-butyl-1-(4-hydroxybenzyl)-2-oxopyrrolidin-3-ylmethyl]formamide (0.13 g, 0.32 mmol) was dissolved in methanol (5 mL) and stirred under a hydrogen balloon in the presence of palladium on activated carbon (30 mg) for 4 h. The reaction mixture was filtered, concentrated and the residue was purified by HPLC to afford the title compound as a white solid (0.071 g, 70%). MS(ES) m/e 321 [M+H]+.

EXAMPLE 5

Preparation of (+/−)-(3RS,4SR)-N-{4-Butyl-1-[4-(furan-2-ylmethoxy)benzyl]-2-oxopyrrolidin-3-yl-methyl}-N-hydroxyformamide 5(a) (+/−)-(3RS,4SR)-N-Benzyloxy-N-{4-butyl-1-[4-(furan-2-ylmethoxy)benzyl]-2-oxo-pyrrolidin-3-yl-methyl}formamide To a solution of (+/−)-(3RS,4SR)-N-benzyloxy-N-[4-butyl-1-(4-hydroxybenzyl)-2-oxopyrrolidin-3-yl-methyl]formamide (0.1 g, 0.24 mmol) in tetrahydrofuran (3 mL) under argon was added furan-2-yl-methanol (0.041 mL, 0.048 mmol) and triphenylphosphine (0.07 g, 0.27 mmol). The solution was cooled to 0° C. and diethyl azodicarboxylate (0.042 mL, 0.27 mmol) was added dropwise. The reaction mixture was warmed up to rt and stirred overnight. The reaction was quenched with saturated aqueous NaHCO₃ (10 mL) and extracted with dichloromethane (3×10 mL). The combined extractions were dried (Na₂SO₄), filtered and concentrated. The residue was purified by flash column chromatography (silica gel, ethyl acetate/hexanes 1:1) to afford (+/−)-(3RS,4SR)-N-benzyloxy-N-{4-butyl-1-[4-(furan-2-yl-methoxy)benzyl]-2-oxopyrrolidin-3-yl-methyl}formamide as a colorless oil (0.075 g, 63%). MS(ES) m/e 491 [M+H]+.

5(b) (+/−)-(3RS,4SR)-N-{4-Butyl-1-[4-(furan-2-yl-methoxy)benzyl]-2-oxopyrrolidin-3-yl-methyl}-N-hydroxyformamide Following the procedure of Example 4(c), (+/−)-(3RS,4SR)-N-{4-butyl-1-[4-(furan-2-yl-methoxy)benzyl]-2-oxopyrrolidin-3-yl-methyl}-N-hydroxyformamide was prepared as a colorless glass. MS(ES) m/e 401 [M+H]+.

Proceeding in a similar manner, but substituting appropriate intermediates for the furan-2-yl-methanol, the following compounds were synthesized:

(+/−)-(3RS,4SR)-N-{4-Butyl-1-[4-(2-morpholin-4-yl-2-oxoethoxy)benzyl]-2-oxopyrrolidin-3-yl-methyl}-N-hydroxyformamide. MS(ES) m/e 448 [M+H]+.

(+/−)-(3RS,4SR)-N-{4-Butyl-1-[4-(4-carboxy-1-butoxy)benzyl]-2-oxopyrrolidin-3-yl-methyl}-N-hydroxyformamide. MS(ES) m/e 407 [M+H]+.

(+/−)-(3RS,4SR)-N-{4-Butyl-1-[4-(3-hydroxybenzoxy)benzyl]-2-oxopyrrolidin-3-yl-methyl}-N-hydroxyformamide. MS(ES) m/e 427 [M+H]+.

(+/−)-(3RS,4SR)-N-{4-Butyl-2-oxo-1-[4-(tetrahydrofuran-2-ylmethoxy)benzyl]pyrrolidin-3-yl-methyl}-N-hydroxyformamide. MS(ES) m/e 405 [M+H]+.

(+/−)-(3RS,4SR)-N-{4-Butyl-1-[4-(3-hydroxypropoxy)benzyl]-2-oxo-yrrolidin-3-yl-methyl}-N-hydroxyformamide. MS(ES) m/e 379 [M+H]+.

(+/−)-(3RS,4SR)-N-{4-Butyl-2-oxo-1-[4-(piperidin-3-yl-methoxy)-benzyl]pyrrolidin-3-yl-methyl}-N-hydroxyformamide. MS(ES) m/e 418 [M+H]+.

(+/−)-(3RS,4SR)-N-{4-Butyl-2-oxo-1-[4-(pyridin-3-yl-methoxy)benzyl]pyrrolidin-3-yl-methyl}-N-hydroxyformamide. MS(ES) m/e 412 [M+H]+.

(+/−)-(3RS,4SR)-N-{4-Butyl-1-[4-(5-hydroxypentoxy)benzyl]-2-oxopyrrolidin-3-yl-methyl}-N-hydroxyformamide. MS(ES) m/e 407 [M+H]+.

EXAMPLE 6

Preparation of (+/−)-(3RS,4SR)-N-(4-Butyl-2-oxo-1-phenylpyrrolidin-3-yl-methyl)-N-hydroxyformamide

6(a) 3-Hydroxymethyl-heptanoic acid phenylamide

To a solution of aniline (0.36 mL, 4.0 mmol) in toluene (10 mL) was added trimethylaluminum in toluene (2M, 2.5 mL, 5 mmol). After 20 min, a solution of (+/−)-4-butyldihydrofuran-2-one (0.4 g, 4 mmol) in toluene (1 mL) was added and the reaction mixture was refluxed for 3 h. The reaction was cooled to 0° C. and carefully quenched with 1 M HCl (15 mL), and then extracted with dichloromethane (3×15 mL). The combined extractions were dried over $Na_2SO_4$, filtered and concentrated. The residue was purified by flash column chromatography (silica gel, ethyl acetate/hexanes 3:2) to afford 3-hydroxymethylheptanoic acid phenylamide as a white solid (0.66 g, 70%). MS(ES) m/e 236 [M+H]+.

6(b) 4-Butyl-1-phenylpyrrolidin-2-one

To a solution of 3-hydroxymethylheptanoic acid phenylamide (0.61 g, 2.6 mmol) in THF (30 mL) under argon was added triphenylphosphine (1.36 g, 5.2 mmol). The solution was cooled to 0° C. and diethyl azodicarboxylate (0.61 mL, 3.9 mmol) was added dropwise. The reaction mixture was warmed up to rt and stirred overnight. The reaction was quenched with saturated aqueous $NaHCO_3$ (50 mL) and extracted with dichloromethane (3×50 mL). The combined extractions were dried ($Na_2SO_4$), filtered and concentrated. The residue was purified by flash column chromatography (silica gel, ethyl acetate/hexanes 1:2) to afford 4-butyl-1-phenylpyrrolidin-2-one as a white solid (0.4 g, 72%). MS(ES) m/e 218 [M+H]+.

6(c) (+/−)-(3RS,4SR)-N-(4-Butyl-2-oxo-1-phenylpyrrolidin-3-yl-methyl)-N-hydroxyformamide Following the procedure of Example 1(e)-1(f), (+/−)-(3RS,4SR)-N-(4-butyl-2-oxo-1-phenylpyrrolidin-3-yl-methyl)-N-hydroxyformamide was prepared as a colorless glass. MS(ES) m/e 291 [M+H]+.

EXAMPLE 7

Preparation of (+/−)-(3RS,4SR)-N-[4-Butyl-2-oxo-1-(t-butylcarboxy)pyrrolidin-3-yl-methyl]-N-hydroxyformamide

7(a) 4-Butyl-2-oxopyrrolidine-1-carboxylic acid tert-butyl ester

To a solution of 4-butylpyrrolidin-2-one (4.1 g, 29.0 mmol) in dry acetonitrile (45 mL) was added triethylamine (6.1 mL, 43.6 mmol), di-tert-butyl dicarbonate (7.6 g, 34.8 mmol) and then 4-dimethylaminopyridine (0.3 g, 2.5 mmol). The reaction was stirred at rt for 4 h. The solvent was removed under vacuum, and the residue was dissolved in ethyl acetate (50 mL) and washed with water (30 mL) and brine (30 mL), dried ($Na_2SO_4$), filtered and concentrated. The residue was purified by flash column chromatography (silica gel, ethyl acetate/hexanes 1:9) to afford 4-butyl-2-oxopyrrolidine-1-carboxylic acid tert-butyl ester as a white solid (5.2 g, 75%). MS(ES) m/e 242 [M+H]+.

7(b) (+/−)-(3RS,4SR)-3-[(Benzyloxyformylamino)methyl]-4-butyl-2-oxopyrrolidin-1-carboxylic acid tert-butyl ester Following the procedures of Example 1(e)-1(f), except omitting the final hydrogenation step, (+/−)-(3RS,4SR)-3-[(benzyloxyformylamino)methyl]-4-butyl-2-oxopyrrolidin-1-carboxylic acid tert-butyl ester was prepared as a colorless oil. MS(ES) m/e 405 [M+H]+.

7(c) (+/−)-(3RS,4SR)-N-[4-Butyl-2-oxo-1-(t-butylcarboxy)pyrrolidin-3-yl-methyl]-N-hydroxyformamide;

Following the procedure of Example 4(c), the title compound was prepared as a colorless glass. MS(ES) m/e 315 [M+H]+.

EXAMPLE 8

Preparation of (+/−)-(3RS,4SR)-N-(4-Butyl-2-oxopyrrolidin-3-yl-methyl)-N-hydroxyformamide

8(a) (+/−)-(3RS,4SR)-N-Benzyloxy-N-(4-butyl-2-oxopyrrolidin-3-yl-methyl)formamide (+/−)-(3RS,4SR)-3-[(Benzyloxyformylamino)methyl]-4-butyl-2-oxopyrrolidin-1-carboxylic acid tert-butyl ester (1.7 g, 4.2 mmol) was dissolved in 5% TFA/1,2-dichloroethane (100 mL) and the reaction was stirred at rt for 3 h. The solvents were removed under vacuum, the residue was dissolved in dichloromethane and washed with saturated aq. $NaHCO_3$. The organic solution was dried ($Na_2SO_4$), filtered and concentrated. The residue was purified by flash column chromatography (silica gel, ethyl acetate) to afford (+/−)-(3RS,4SR)-N-benzyloxy-N-(4-butyl-2-oxopyrrolidin-3-yl-methyl)formamide as a white solid (0.95 g, 74%). MS(ES) m/e 305 [M+H]+.

8(b) (+/−)-(3RS,4SR)-N-(4-Butyl-2-oxopyrrolidin-3-yl-methyl)-N-hydroxyformamide Following the procedure of Example 4(c), (+/−)-(3RS,4SR)-N-(4-butyl-2-oxopyrrolidin-3-yl-methyl)-N-hydroxyformamide was prepared as a colorless glass. MS(ES) m/e 215 [M+H]+.

EXAMPLE 9

Preparation of (+/−)-(3RS,4SR)-N-[4-Butyl-2-oxo-1-(1-phenylmethanoyl)pyrrolidin-3-yl-methyl]-N-hydroxyformamide

9(a) (+/−)-(3RS,4SR)-N-Benzyloxy-N-[4-butyl-2-oxo-1-(1-phenylmethanoyl)pyrrolidin-3-yl-methyl]formamide To a solution of (+/−)-(3RS,4SR)-N-benzyloxy-N-(4-butyl-2-oxopyrrolidin-3-yl-methyl)formamide (0.18 g, 0.59 mmol) in dry THF (3 mL) at −78° C. under argon was added dropwise lithium bis(trimethylsilyl)amide in THF (1 M, 0.71 mL). After 20 min, benzoyl chloride (0.077 mL, 0.89 mmol) was added dropwise and stirring continued for 2 h. The reaction was warmed up to 0° C., quenched with saturated aq. $NH_4Cl$ (10 mL) and extracted with dichloromethane (3×10 mL). The combined organic solution was dried ($Na_2SO_4$), filtered and concentrated. The residue was purified by flash column chromatography (silica gel, ethyl acetate/hexanes 1:1) to afford (+/−)-(3RS,4SR)-N-benzyloxy-N-[4-butyl-2-oxo-1-(1-phenylmethanoyl)pyrrolidin-3-yl-methyl)formamide as a white solid (0.12 g, 50%). MS(ES) m/e 409 [M+H]+.

9(b) (+/−)-(3RS,4SR)-N-[4-Butyl-2-oxo-1-(1-phenylmethanoyl)pyrrolidin-3-yl-methyl]-N-hydroxyformamide Following the procedure of Example 4(c), (+/−)-(3RS, 4SR)-N-[4-butyl-2-oxo-1-(1-phenylmethanoyl)pyrrolidin-3-yl-methyl]-N-hydroxyformamide was prepared as a colorless glass. MS(ES) m/e 319 [M+H]+.

Proceeding in a similar manner, but substituting appropriate intermediates for those listed above, the following compounds were synthesized:

(+/−)-(3RS,4SR)-N-(4-Butyl-2-oxo-1-pentanoylpyrrolidin-3-yl-methyl)-N-hydroxyformamide. MS(ES) m/e 299 [M+H]+.

(+/−)-(3RS,4SR)-N-[4-Butyl-2-oxo-1-(2-phenylethanoyl)pyrrolidin-3-yl-methyl]-N-hydroxyformamide. MS(ES) m/e 333 [M+H]+.

(+/−)-(3RS,4SR)-N-(1-Benzenesulfonyl-4-butyl-2-oxopyrrolidin-3-yl-methyl)-N-hydroxyformamide. MS(ES) m/e 355 [M+H]+.

(+/−)-(3RS,4SR)-N-[1-(Butane-1-sulfonyl)-4-butyl-2-oxopyrrolidin-3-yl-methyl]-N-hydroxyformamide. MS(ES) m/e 335 [M+H]+.

(+/−)-(3RS,4SR)-N-[4-Butyl-1-(naphthalen-2-yl-methanoyl)-2-oxopyrrolidin-3-yl-methyl]-N-hydroxyformamide. MS(ES) m/e 369 [M+H]+.

(+/−)-(3RS,4SR)-N-{4-Butyl-1-[1-(4-ethoxyphenyl)methanoyl]-2-oxopyrrolidin-3-yl-methyl}-N-hydroxyformamide. MS(ES) m/e 363 [M+H]+.

(+/−)-(3RS,4SR)-N-{4-Butyl-1-[1-(3-ethoxyphenyl)methanoyl]-2-oxopyrrolidin-3-yl-methyl}-N-hydroxyformamide. MS(ES) m/e 363 [M+H]+.

(+/−)-(3RS,4SR)-N-{4-Butyl-1-[1-(2-ethoxyphenyl)methanoyl]-2-oxopyrrolidin-3-yl-methyl}-N-hydroxyformamide. MS(ES) m/e 363 [M+H]+.

(+/−)-(3RS,4SR)-N-{4-Butyl-1-[2-(2-hydroxyphenyl)-2-oxoethyl]-2-oxopyrrolidin-3-yl-methyl}-N-hydroxyformamide. MS(ES) m/e 349 [M+H]+.

EXAMPLE 10

Preparation of N-((3S,4R)-4-Butyl-1-{(S)-1-[1-(dimethylamino)methanoyl]-3,3dimethylbutyl}-2-oxopyrrolidin-3-yl-methyl)-N-hydroxyformamide 10(a) (3S,4R)-3-Benzyloxymethyl-4-butyldihydrofuran-2-one (R)-3-Hydroxymethylheptanoic acid, (S)-1-phenylethylamide (8.4 g, 31.9 mmol) was dissolved in 1 M H2SO4/dioxane (1:1, 110 mL) and the resulting solution was refluxed overnight under argon. After cooling to rt, the reaction mixture was diluted with ethyl acetate/hexanes (1:3, 200 mL) and washed with water (2×100 mL), saturated aq. NaHCO3 (2×100 mL), and brine (100 mL). The solution was dried (Na2SO4), filtered, and concentrated to afford pure (R)-4-butyldihydrofuran-2-one as a colorless oil (3.5 g, 78%).

To a solution of diisopropylamine (1.28 mL, 9.1 mmol) in dry THF (15 mL) at 0° C. was dropwise added n-butyl lithium (1.6 M, 8.4 mmol). After 30 min, the solution was cooled to −78° C. and (R)-4-butyldihydrofuran-2-one (1.0 g, 7.0 mmol) was added slowly. The mixture was stirred for an additional 30 min. Trimethylsilyl chloride (1.78 mL, 14 mmol) was rapidly added and the mixture was gradually warmed up to rt during a period of 3 h. The reaction mixture was concentrated under vacuum, and hexanes (15 mL) was added to the residue. Rapid filtration and removal of the solvent under vacuum yielded crude t-butyl-[(R)-4-butyl-4,5-dihydrofuran-2-yloxy]silane as a colorless oil (1.32 g, 88%). This crude intermediate was dissolved in dry dichloromethane (20 mL) under argon. The solution was cooled to 0° C. and treated with benzyloxymethyl chloride (1.5 mL, 10 mmol) followed by zinc bromide (20 mg). The reaction was warmed up to rt and stirred overnight.

Aqueous work-up and purification by flash column chromatography (silica gel, ethyl acetate/hexanes 1:6) afforded (3S, 4R)-3-benzyloxymethyl-4-butyldihydrofuran-2-one as a colorless oil (1.1 g, 66%). MS(ES) m/e 263 [M+H]+.

10(b) (2S,3R)-2-Benzyloxymethyl-3-hydroxymethylheptanoic acid [(S)-dimethylcarbamoyl-dimethylpropyl]amide (3S,4R)-3-Benzyloxymethyl-4-butyldihydrofuran-2-one (0.2 g, 0.76 mmol), (S)-2-amino-3,3,N,N-tetramethylbutyramide (0.5 g, 3.16 mmol) and 2-hydroxypyridine (0.073 g, 0.76 mmol) were mixed in a sealed tube under argon and heated to 80° C. for 36 h. After cooling to rt, the reaction mixture was treated with 1 M HCl (20 ml) and extracted with ethyl acetate (4×30 mL). Removal of the solvent under vacuum and purification of the residue by HPLC afforded (2S,3R)-2-benzyloxymethyl-3-hydroxymethylheptanoic acid [(S)-dimethylcarbamoyl-dimethylpropyl]amide as a white solid (0.14 g, 44%). MS(ES) m/e 421 [M+H]+.

10(c) (S)-2-[(3S,4R)-3-Benzyloxymethyl-4-butyl-2-oxopyrrolidin-1-yl]-3,3,N,N-tetramethyl butyramide To a solution of (2S,3R)-2-benzyloxymethyl-3-hydroxymethylheptanoic acid [(S)-dimethylcarbamoyl-dimethylpropyl]amide (0.14 g, 0.33 mmol) in THF (2 mL) under argon was added a premixed solution of tributylphosphine (0.12 mL, 0.48 mmol) and di-t-butyl azodicarboxylate (0.11 g, 0.48 mmol) in THF (1 mL) at 0° C. The reaction was warmed up to rt and stirred overnight. Aqueous work-up and purification of the residue by HPLC afforded (S)-2-[(3S,4R)-3-benzyloxymethyl-4-butyl-2-oxopyrrolidin-1-yl]-3,3, N,N-tetramethyl butyramide as a white solid (0.08 g, 60%). MS(ES) m/e 403 [M+H]+.

10(d) (S)-2-[(3S,4R)-3-Benzyloxyiminomethyl-4-butyl-2-oxopyrrolidin-1-yl]-3,3,N,N-tetramethyl butyramide (S)-2-[(3S,4R)-3-Benzyloxymethyl-4-butyl-2-oxopyrrolidin-1-yl]-3,3, N,N-tetramethyl butyramide (0.08 g, 0.2 mmol) was dissolved in methanol (2 mL) and stirred overnight under a hydrogen balloon in the presense of palladium on activated carbon (15 mg). Filtration followed by concentration provided a crude alcohol (58 mg) which was dissolved in dichloromethane (5 mL) and treated with Dess-Martin periodinane (0.13 g, 0.3 mmol) at 0° C. After warning up to rt, the reaction was stirred overnight and the solvent was removed under vacuum. The residue was then dissolved in pyridine (5 mL) and benzyloxyamine hydrochloride (0.064 g, 0.4 mmol) was added. After 1 h, the reaction mixture was condensed to dryness, the residue was dissolved in 1 N aq.

NaOH/dichloromethane (2:3, 15 mL). The organic phase was separated, the aqueous phase was extracted with dichloromethane (5 mL). The combined organic extracts were dried (Na$_2$SO$_4$), filtered and concentrated. Purification of the residue by HPLC afforded (S)-2-[(3S,4R)-3-benzyloxyiminomethyl-4-butyl-2-oxopyrrolidin-1-yl]-3,3,N,N-tetramethyl butyramide as a colorless oil (0.05 g, 61%). MS(ES) m/e 416 [M+H]$^+$.

10(e) N-((3S,4R)-4-Butyl-1-{(S)-1-[1-(dimethylamino)methanoyl]-3,3-dimethylbutyl}-2-oxopyrrolidin-3-yl-methyl)-N-hydroxyformamide Following the procedures of 1(e)-1(f), beginning with the sodium cyanoborohydride reduction, N-((3S,4R)-4-Butyl-1-{(S)-1-[1-(dimethylamino)methanoyl]-3,3-dimethylbutyl}-2-oxopyrrolidin-3-yl-methyl)-N-hydroxyformamide was prepared as a colorless glass. MS(ES) m/e 356 [M+H]$^+$.

Proceeding in a similar manner, but substituting appropriate intermediates for the ones listed above, the following compounds were synthesized:

N-((3S,4R)-4-Butyl-1-{(S)-1-[1-((S)-2-methoxymethyl-pyrrolidin-1-yl)-methanoyl]-3-methyl-butyl}-2-oxo-pyrrolidin-3-yl-methyl)-N-hydroxyformamide. MS(ES) m/e 426 [M+H]$^+$.

N-((3R,4S)-4-Butyl-1-{(S)-1-[1-((S)-2-methoxymethyl-pyrrolidin-1-yl)-methanoyl]-3-methyl-butyl}-2-oxo-pyrrolidin-3-yl-methyl)-N-hydroxyformamide. MS(ES) m/e 426 [M+H]$^+$.

With appropriate manipulation and protection of any chemical functionality, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals, it is normally formulated in accordance with standard pharmaceutical practice as a pharmaceutical composition.

The present compounds are useful for the treatment of bacterial infections including, but not limited to, respiratory tract infections and/or Gram positive infections.

Compounds of Formula (I) and their pharmaceutically acceptable salts may be administered in a standard manner for antibiotics, for example orally, parenterally, sub-lingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free acid. Each dosage unit for intranasal administration contains suitably 1-400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay:

*S. aureus* or *E. coli* PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp. 180-182, with minor modifications. The reaction mixture is contained in 50 uL with 50 mM potassium phosphate buffer (pH 7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility

Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Staphylococcus aureus* WCUH29, *Enterococcus faecalis* I, *Enterococcus faecalis* 7, *Haemophilus influenzae* Q1, *Haemophilus influenzae* NEMC1, *Moraxella catarrhalis* 1502, *Streptococcus pneumoniae* 1629, *Streptococcus pneumoniae* N1387, *Streptococcus pneumoniae* N1387, *E. coli* 7623 (AcrABEFD+) and *E. coli* 120 (AcrAB−). The minimum inhibitory concentration (MIC) was determined as the lowest concentration of compound that inhibited visible growth. A mirror reader was used to assist in determining the MIC endpoint.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A compound according to formula (I):

(I)

wherein

R1 is selected from the group consisting of: $C_{1-6}$alkyl, —$C_{1-2}$alkylAr, and Ar;

R2 is selected from the group consisting of hydrogen, $C_{1-6}$alkyl, —$(CH_2)_m$OH, —$(CH_2)_n$Ar', —$SO_2$R3, —C(O)R3, —C(O)NHR3, —C(O)OR3, —CH(R4)CONR5R6, and —CH(R4)CO$_2$R7;

R3 is selected from the group consisting of $C_{1-6}$alkyl, —$C_{1-2}$alkylAr', and Ar';

R4 is hydrogen or $C_{1-6}$alkyl;

R5 and R6 are independently selected from the group consisting of hydrogen and $C_{1-6}$alkyl;

R7 is selected from the group consisting of hydrogen and $C_{1-3}$alkyl;

Ar is selected from the group consisting of phenyl, furyl, and thienyl, all of which may be optionally substituted by one or more $Z_1$ groups;

Ar' is selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidyl, all of which may be optionally substituted by one or more $Z_2$ groups;

$Z_1$ is independently selected from the group consisting of hydrogen, $C_{1-3}$alkyl, —CN, F, Cl, Br, and I;

$Z_2$ is independently selected from the group consisting of hydrogen, $C_{1-6}$alkyl, $C_{1-6}$alkoxy, —$(CH_2)_n$CO$_2$R4, —C(O)NR5R6, —CN, —$(CH_2)_n$OH, —NO$_2$, F, Cl, Br, I, —NR5R6, and —NHC(O)R1;

m is 2 to 5; and n is 0 to 5; or a pharmaceutically acceptable salt thereof.

2. A compound selected from the group consisting of:

N-[(3S,4R)-4-Butyl-1-(5-hydroxypentyl)-2-oxopyrrolidin-3-yl-methyl]-N-hydroxyformamide;

N-[(3R,4S)-4-Butyl-1-(5-hydroxypentyl)-2-oxopyrrolidin-3-yl-methyl]-N-hydroxyformamide;

(+/−)-(3RS,4SR)-N-[4-Butyl-2-oxo-1-(t-butylcarboxy)pyrrolidin-3-yl-methyl]-N-hydroxyformamide;

(+/−)-(3RS,4SR)-N-(4-Butyl-2-oxopyrrolidin-3-yl-methyl)-N-hydroxyformamide;

(+/−)-(3RS,4SR)-N-(4-Butyl-2-oxo-1-pentanoylpyrrolidin-3-yl-methyl)-N-hydroxyformamide;

(+/−)-(3RS,4SR)-N-[4-Butyl-2-oxo-1-(2-phenylethanoyl)pyrrolidin-3-yl-methyl]-N-hydroxyformamide;

(+/−)-(3RS,4SR)-N-[4-Butyl-2-oxo-1-(1-phenylmethanoyl)pyrrolidin-3-yl-methyl]-N-hydroxyformamide;

(+/−)-(3RS,4SR)-N-(1-Benzenesulfonyl-4-butyl-2-oxopyrrolidin-3-yl-methyl)-N-hydroxyformarnide;

(+/−)-(3RS,4SR)-N-[1-(Butane-1-sulfonyl)-4-butyl-2-oxopyrrolidin-3-yl-methyl]-N-hydroxyformamide;

(+/−)-(3RS,4SR)-N-[4-Butyl-1-(naphthalen-2-ylmethanoyl)-2-oxopyrrolidin-3-yl-methyl]-N-hydroxyformamide;

(+/−)-(3RS,4SR)-N-(1-Benzyl-4-butyl-2-oxopyrrolidin-3-yl-methyl)-N-hydroxyformnamide;

(+/−)-(3RS,4SR)-N-{4-Butyl-1-[1-(4-ethoxyphenyl)methanoyl]-2-oxopyrrolidin-3-yl-methyl}-N-hydroxyformamide;

(+/−)-(3RS,4SR)-N-{4-Butyl-1-[1-(3-ethoxyphenyl)methanoyl]-2-oxopyrrolidin-3-yl-methyl}-N-hydroxyformamide;

(+/−)-(3RS,4SR)-N-{4-Butyl-1-[1-(2-ethoxyphenyl)methanoyl]-2-oxopyrrolidin-3-yl-methyl}-N-hydroxyformamide;

(+/−)-(3RS,4SR)-N-(4-Butyl-2-oxo-1-pyridin-3-ylmethylpyrrolidin-3-yl-methyl)-N-hydroxyformamide;

N-((3S,4R)-4-Butyl-1-{(S)-1-[1-((S)-2-methoxymethylpyrrolidin-1-yl)methanoyl]-3-methylbutyl}-2-oxopyrrolidin-3-yl-methyl)-N-hydroxyformamide;

N-((3R,4S)-4-Butyl-1-{(S)-1-[1-((S)2-methoxymethylpyrrolidin-1-yl)-methanoyl]-3-methylbutyl}-2-oxopyrrolidin-3-yl-methyl)-N-hydroxyformamide;

N-((3S,4R)-4-Butyl-1-{(S)-1-[1-(dimethylamino)methanoyl]-3,3-dimethylbutyl}-2-oxopyrrolidin-3-yl-methyl)-N-hydroxyformamide;

(+/−)-(3RS,4SR)-N-[4-Butyl-1-(4-ethoxybenzyl)-2-oxopyrrolidin-3-yl-methyl]-N-hydroxyformamide;

(+/−)-(3RS,4SR)-N-[4-Butyl-1-(4-hydroxybenzyl)-2-oxopyrrolidin-3-yl-methyl]-N-hydroxyformamide;

(+/−)-(3RS,4SR)-N-{4-Butyl-1-[4-(2-morpholin-4-yl-2-oxoethoxy)benzyl]-2-oxopyrrolidin-3-yl-methyl}-N-hydroxyformamide;

(+/−)-(3RS,4SR)-N-{4-Butyl-1-[4-(4-carboxy-1-butoxy)benzyl]-2-oxopyrrolidin-3-yl-methyl}-N-hydroxyformamide;

(+/−)-(3RS,4SR)-N-{4-Butyl-1-[4-(3-hydroxybenzoxy)benzyl]-2-oxopyrrolidin-3-yl-methyl}-N-hydroxyformamide;

(+/−)-(3RS,4SR)-N-{4-Butyl-2-oxo-1-[4-(tetrahydrofuran-2-ylmethoxy)benzyl]pyrrolidin-3-yl-methyl}-N-hydroxyformamide;

(+/−)-(3RS,4SR)-N-{4-Butyl-1-[4-(furan-2-ylmethoxy)benzyl]-2-oxopyrrolidin-3-yl-methyl}-N-hydroxyformamide;

(+/−)-(3RS,4SR)-N-{4-Butyl-1-[4-(3-hydroxypropoxy)benzyl]-2-oxopyrrolidin-3-yl-methyl}-N-hydroxyformamide;

(+/−)-(3RS,4SR)-N-{4-Butyl-2-oxo-1-[4-(piperidin-3-ylmethoxy)benzyl]pyrrolidin-3-yl-methyl}-N-hydroxyformamide;

(+/−)-(3RS,4SR)-N-{4-Butyl-2-oxo-1-[4-(pyridin-3-ylmethoxy)benzyl]pyrrolidin-3-yl-methyl}-N-hydroxyformamide;

(+/−)-(3RS,4SR)-N-{4-Butyl-1-[4-(5-hydroxypentoxy)benzyl]-2-oxopyrrolidin-3-yl-methyl}-N-hydroxyformamide;

(+/−)-(3RS,4SR)-N-[4-Butyl-1-(2,3-dichlorobenzyl)-2-oxopyrrolidin-3-yl-methyl]-N-hydroxyformamide;

(+/−)-(3RS,4SR)-N-[4-Butyl-1-(3,4-dichlorobenzyl)-2-oxopyrrolidin-3-yl-methyl]-N-hydroxyformamide;

(+/−)-(3RS,4SR)-N-(4-Butyl-2-oxo-1-phenylpyrrolidin-3-yl-methyl)-N-hydroxyformamide;

(+/−)-(3RS,4SR)-N-{4-Butyl-1-[2-(2-hydroxyphenyl)-2-oxoethyl]-2-oxopyrrolidin-3-yl-methyl}-N-hydroxyformamide;

(+/−)-(3RS,4SR)-N-[4-Butyl-1-(3,5-dimethylisoxazol-4-ylmethyl)-2-oxopyrrolidin-3-yl-methyl]-N-hydroxyformamide; and (+/−)-(3RS,4SR)-N-[4-Butyl-1-(2-methylthiazol-4-ylmethyl)-2-oxopyrrolidin-3-yl-methyl]-N-hydroxyformamide; or a pharmaceutically acceptable salt thereof.

3. A pharmaceutical composition comprising a compound according to claim 1 or a pharmaceutically acceptable salt thereof and a pharmaceutically acceptable carrier.

4. A compound according to claim 1 wherein:
R1 is $C_{1-6}$alkyl;
R2 is selected from the group consisting of hydrogen, —$(CH_2)_m$OH, —$(CH_2)_n$Ar', —$SO_2$R3, —C(O)R3, —C(O)OR3, and —CH(R4)CONR5R6;
R3 is selected from the group consisting of $C_{1-6}$alkyl, —$C_{1-2}$alkylAr', and Ar';
R4 is hydrogen or $C_{1-6}$alkyl;
R5 and R6 are $C_{1-6}$alkyl;
Ar' is selected from the group consisting of phenyl, naphthyl, pyridyl, thiazolidinyl, and isoxazolyl, all of which may be optionally substituted by one or more $Z_2$ groups;
$Z_2$ is independently selected from the group consisting of $C_{1-6}$alkyl, $C_{1-6}$alkoxy, —C(O)NR5R6, —$(CH_2)_n$OH, and Cl;
m is 5; and
n is 0 or 1; or a pharmaceutically acceptable salt thereof.

5. A compound according to claim 4 wherein R1 is butyl; or a pharmaceutically acceptable salt thereof.

6. A method of treating a bacterial respiratory tract infection comprising administering to a subject in need of treatment a compound according to claim 1 or a pharmaceutically acceptable salt thereof.

7. A method of treating a bacterial respiratory tract infection comprising administering to a subject in need of treatment a compound according to claim 4 or a pharmaceutically acceptable salt thereof.

8. A method of treating a bacterial respiratory tract infection comprising administering to a subject in need of treatment a compound according to claim 5 or a pharmaceutically acceptable salt thereof.

9. A method of treating a *Haemophilus influenzae*, *Moraxella catarrhalis*, or *Streptococcus pneumoniae* infection comprising administering to a subject in need of treatment a compound according to claim 1 or a pharmaceutically acceptable salt thereof.

10. A method of treating a *Haemophilus influenzae*, *Moraxella catarrhalis*, or *Streptococcus pneumoniae* infection comprising administering to a subject in need of treatment a compound according to claim 4 or a pharmaceutically acceptable salt thereof.

11. A method of treating a *Haemophilus influenzae*, *Moraxella catarrhalis*, or *Streptococcus pneumoniae* infection comprising administering to a subject in need of treatment a compound according to claim 5 or a pharmaceutically acceptable salt thereof.

12. A pharmaceutical composition comprising a compound according to claim 4 or a pharmaceutically acceptable salt thereof and a pharmaceutically acceptable carrier.

13. A pharmaceutical composition comprising a compound according to claim 5 or a pharmaceutically acceptable salt thereof and a pharmaceutically acceptable carrier.

* * * * *